US006667035B1

(12) United States Patent
Von Eichel-Streiber et al.

(10) Patent No.: US 6,667,035 B1
(45) Date of Patent: Dec. 23, 2003

(54) AMINO ACID SEQUENCES FOR THERAPEUTIC AND PROPHYLACTIC USE AGAINST DISEASES DUE TO CLOSTRIDIUM DIFFICILE TOXINS

(75) Inventors: Christoph Von Eichel-Streiber, Bingerweg 15, Schweppenhausen (DE), 55444; Michael Moos, Mainz (DE)

(73) Assignee: Christoph Von Eichel-Streiber (DE)

( * ) Notice: Subject to any disclaimer, the term of this patent is extended or adjusted under 35 U.S.C. 154(b) by 0 days.

(21) Appl. No.: 09/508,413

(22) PCT Filed: Sep. 10, 1998

(86) PCT No.: PCT/EP98/05759

§ 371 (c)(1),
(2), (4) Date: May 27, 2000

(87) PCT Pub. No.: WO99/12971

PCT Pub. Date: Mar. 18, 1999

(30) Foreign Application Priority Data

Sep. 10, 1997 (DE) .......................................... 197 39 685

(51) Int. Cl.$^7$ ...................... A61K 39/395; A61K 39/40; A61K 39/42; C07K 1/00; C07K 16/00
(52) U.S. Cl. ................................ 424/130.1; 424/141.1; 424/150.1; 424/164.1; 424/167.1; 530/350; 530/387.1; 530/388.1; 530/388.2; 530/388.4; 530/389.5
(58) Field of Search .............................. 530/350, 387.1, 530/388.2, 389.5, 88.1, 388.4; 424/130.1, 141.1, 150.1, 164.1, 167.1

(56) References Cited

U.S. PATENT DOCUMENTS

| 4,879,218 A | 11/1989 | Wilkins et al. |
| 5,071,759 A | 12/1991 | Rothman et al. |
| 5,098,826 A | 3/1992 | Wilkins et al. |

FOREIGN PATENT DOCUMENTS

| EP | 153519 A1 B1 | 9/1985 |
| EP | 171496 A2 B1 | 2/1986 |
| EP | 173494 A2 | 3/1986 |
| EP | 184187 A2 | 6/1986 |
| EP | 209273 A1 B1 | 1/1987 |
| EP | 411893 A2 A3 | 2/1991 |
| WO | WO 91/10737 A1 | 7/1991 |
| WO | WO 91/18293 A1 | 11/1991 |
| WO | WO 92/07075 A1 | 4/1992 |
| WO | 92/11383 * | 7/1992 |
| WO | 95/06067 * | 3/1995 |
| WO | WO 96/12802 A1 | 5/1996 |

OTHER PUBLICATIONS

Goshorn et al (J. of Biol. Chem. vol. 266, No. 4, pp 2134–2142), Feb. 5, 1991.*
Miodzik et al (Cell vol. 60, pp 211–224), Jan. 26, 1990.*

Barroso, L. et al. (1994). "Mutagenesis of the *Clostridium difficile* Toxin B Gene and Effect on Cytotoxic Activity," *Micro. Patho.* 16(4):297–303.

Benhar, I. et al. (Dec. 1994). "Rapid Humanization of the Fv of Monoclonal Antibody B3 by Using Framework Exchange of the Recombinant Immunotoxin B3 (Fv)–PE38," *Proc. Natl. Acad. Sci.* 91:12051–12055.

Corthier, G. et al. (Mar. 1991). "Protection Against Experimental Pseudomembranous Colitis in Gnotobiotic Mice by Use of Monoclonal Antibodies Against *Clostridium difficile* Toxin A," *Infec. and Imm.* 59(3):1192–1195.

Düring, K. (1988). "Wound–Inducible Expression and Secretion of T4 Lysozyme and Monoclonal Antibodies in *Nicotiana Tabacum*," Inaugral Dissertation to Obtain a Doctorate at the Mathematisch–Naturwissenchaftlichen Fakultät der Universität zu Köln. Köln ed. pp. 1–90. (English Translation attached).

Freer, J. et al. eds. Jun. 27–Jul. 2, 1993). *Bacterial Protein Toxins*. Sixth European Workshop, Gustav Fischer Verlag: New York, (Table of Contents only). 12 pages total.

Kettleborough, C. et al. (1993). "Optimization of Primers for Cloning Libraries of Mouse Immunoglobulin Genes Using the Polymerase Chain Reaction," *Eur. J. Imm.* 23:206–211.

Kink, J. and Williams, J. (May 1998). "Antibodies to Recombinant *Clostridium difficile* Toxins A and B are an Effective Treatment and Prevent Relapse of *C. difficile*–Associated Disease in a Hamster Model of Infection," *Infec. and Imm.* 66(5):2018–2025.

Lewis, A. and Crowe, J. et al. (1991). "Immunoglobulin Complementarity–Determining Region Grafting Polymerase Chain Reaction to Generate Humanised Monoclonal Antibodies," *Gene* 101(2):297–302.

Lyerly, D. et al. (1990). "Vaccination Against Lethal *Clostridium difficile* Enterocolitis with a Nontoxic Recombinant Peptide of Toxin A," *Curr. Microbiol.* 21:29–32.

Sato, K. et al. (1994). "Humanization of a Mouse Anti–Human Interleukin–6 Receptor Antibody Comparing Two Methods for Selecting Human Framework Regions," *Mol. Immunol.* 31:371–381.

Sauerborn, M. et al. (1997). "The C–Terminal Ligand–Binding Domain of *Clostridium difficile* Toxin A (TcdA) Abrogates TcdA–Specific Binding to Cells and Prevents Mouse Lethality," *FEMS Microbiol. Letts.* 155:45–54.

(List continued on next page.)

*Primary Examiner*—Mark Navarro
(74) *Attorney, Agent, or Firm*—Morrison & Foerster LLP

(57) ABSTRACT

The invention relates to monoclonal antibodies capable of recognizing and neutralizing epitopes from the ligand domain, the translocation domain or the catalytic domain of the enterotoxin (toxin A) and cytotoxin (toxin B) from *Clostridium difficile*, as well as their production and therapeutical and prophylactic applications to diseases due to the toxins.

16 Claims, No Drawings

OTHER PUBLICATIONS

Skerra, A. (1994). "A General Vector, pASK84, for Cloning, Bacterial Production, and Single–Step Purification of Antibody $F_{ab}$ Fragments," *Gene* 141:79–84.

Stephens, S. et al. (1995). "Comprehensive Pharmacokinetics of a Humanized Antibody and Analysis of Residual Anti–idiotypic Responses," *Immunol.* 85:668–674.

von Eichel–Streiber, C. et al. (Oct. 1996). "Large Clostridial Cytotoxins—a Family of Glycosyltransferases Modifying Small GTP–Binding Proteins," *Trends in Microbiol.* 4(10):375–382.

Ward, S. et al. (1997). "Delivery of Non–Toxic Fragments of *Clostridium difficile* Toxin A to the Mucosal Immune System," *Rev. Med. Microbiol.* 8(Suppl. 1):S34–S36.

* cited by examiner

AMINO ACID SEQUENCES FOR THERAPEUTIC AND PROPHYLACTIC USE AGAINST DISEASES DUE TO *CLOSTRIDIUM DIFFICILE* TOXINS

The object of the invention are amino acid sequences (peptides) produced from antibody producing cells, particularly monoclonal antibody producing hybridoma cells, that neutralize the effect of the *Clostridium difficile* enterotoxin and/or cytotoxin. In addition, there is a description of humanized, monoclonal antibodies for use against the *Clostridium difficile* toxins, as well as the hypervariable regions of these antibodies. Finally a process for the production and application of these amino acid sequences (peptides) and monoclonal antibodies is shown.

It is known that the introduction of macrolide antibiotics such as Clindamycin leads to severe bowel diseases, which manifest themselves as diarrhoea, proceeding further to occasionally fatal pseudomembranous colitis (PMC). This connection gave the disease the name "Clindamycin associated diarrhoea". We now know that nearly all the antibiotics and cytostatic agents used in medicine can trigger the clinical symptoms of PMC.

PMC is characterised clinically by severe diarrhoea that may lead to death due to heavy electrolyte and liquid losses. Depending on the severity of the symptoms, abdominal pain, bloody diarrhoea, fever and leukocytosis occur. Treatment has hitherto consisted in stopping of the administration of the antibiotic causing the disease, by the administration of Vancomycin, as well as balancing liquid and electrolyte losses.

The aetiological agent of pseudomembranous colitis was for a long time unknown. Only in 1977 could hitherto unknown toxic activity be demonstrated in a stool specimen, inducing a cytotoxic effect on CHO cells (Chinese hamster ovary carcinoma cells). Through further investigations it could finally be proved that the pseudomembranous colitis was caused by *Clostridium difficile* and its toxins. *Clostridium difficile* is an obligate anaerobic, gram-positive rod bacteria that builds subterminal oval spores. It is characterised biochemically by being able to ferment monosaccharides such as glucose, N-acetylglucosamine and N-acetylneuraminic acid, but not mannose, xylose or arabinose. *Clostridium difficile* is also not able to split these monosaccharides off from the side chains of the gastrointestinal mucin as enzymes such as neuraminidase, beta-galactosidase or sialidase are missing. Due to these biochemical shortcomings *Clostridium difficile* cannot flourish in the stomach of healthy individuals. If the gut flora are disturbed through the administration of antibiotics or cytostatic agents, *Clostridium difficile* outgrows the gut flora, leading to PMC.

*Clostridium difficile* produces two major factors of pathogenicity, the enterotoxin (toxin A) and the cytotoxin (toxin B). Their production, purification and properties, together with their use to produce monoclonal antibodies are described in detail in European patents 153 519 and 209 273, U.S. Pat. Nos. 4,879,218 and 5,098,826 as well as international patent application WO 91/18 293.

Antibodies clearly play an important part in protecting against the consequences of infection with *Clostridium difficile*. Antibody titres against toxin A and toxin B could be established in patients suffering from PMC. After antibiotic treatment and infection with toxinogenic *Clostridium difficile* strains, hamsters develop the symptoms of PMC and die of it. Prior immunisation of the animals with the above-mentioned toxins protects them from disease. The toxins can be neutralised by antibodies, which are directed against the C-terminal repetitive ligand domains, the central translocation domain or the N-terminal catalytic domain (see reference [1] of the bibliography regarding domain structure). The antibodies directed against the C-terminal repetitive ligand domains hinder the binding of the toxins to the cell receptors, the antibodies directed against the N-terminal catalytic domain block the glucosylation reaction imparted by the toxins, while the antibodies directed against the central translocation domain restrain the translocation of toxins into the cell.

Antibodies neutralising toxin A and/or toxin B thus offer a possible therapy and/or prophylaxis for *Clostridium difficile* diseases in which they do not eliminate the bacteria but they block the action of the toxins produced. In this way the development of the symptoms of the disease can be hindered by acting on the toxins responsible.

Taking toxin A as an example, the cell line DSM ACC 2322 produces an antibody TTC8, which not only binds to toxin A, but is also able to neutralise its biological action. The binding site of TTC8 in toxin A was identified within the repetitive ligand domain. By binding of the antibodies to the toxins, their interaction with the cell receptors is. hindered. The binding site of mAb TTC8 is within amino acids 2480–2539 of toxin A with the (probable) antigen sequence TINGKKYYF (SEQ ID No. 17). A mAb PCG-4 known from U.S. Pat. No. 4,879,218 binds to a defined protein fragment through the amino acids 2098 to 2141 of toxin A.

The mAb 2CV produced by the cells DSM ACC 2321 also binds to a sequence of the ligand domain, in this case of toxin B. The binding occurs in a protein fragment between aa 2233 and 2366 of toxin B. Both monoclonal antibody PCG-4 and monoclonal antibody TCC8 are mouse antibodies, which are not used in therapy on humans but would be suitable as a diagnostic aid.

The monoclonal antibodies generated in the laboratory of the inventor and their reactivities are indicated below:

| Directed against | toxin A[a] | Toxin B[a] |
|---|---|---|
| Catalytic domain[b] | 1212 | 2612, 2688, 3110 1502, 1115 |
| Translocation domain[b] | 2825, 2836, 5288 | 2703, 2740, 2747, 2754, 5288, 2784, 2788 |
| ligand domain[b] | 2620, TTC8 | 2912, 2914, 2916, 2926, 2562, 2CV |

Notes:
[a] The antibodies recognise recombinant protein of the listed regions in the Western blot procedure.
[b] The amino acid position of the domains in toxins A and (B) are: catalytic domain: 1–879 (1–877); translocation domain: 880–1848 (878–1850); ligand domain: 1849–2681 (1851–2360).

All the hitherto generated and described toxin specific monoclonal antibodies were obtained from mice. Therapeutic or prophylactic use of these antibodies in species other than mice (humans or other animals) is not possible since the antibodies are recognised as from a different species, and induce an immune reaction through which they are inactivated. Their adaptation to other species, particularly to humans, has not hitherto been possible since their variable and hypervariable regions were not sequenced (i.e. were not defined).

The objective of the invention was to provide peptides which possess toxin neutralising properties but no longer contain a strongly immunogenic portion, so the peptide is suitable for use in human and veterinary medicine. The neutralisation of the toxin's effect is based on the binding of the antibodies through the attachment of the antibody variable regions to the respective toxin. This binding is mainly determined through the hypervariable regions (or CDR, complementarity determining regions). It was therefore necessary to identify the regions (variable and hypervariable (CDR)) responsible for binding and neutralising the toxins, and to adapt them in such a way that they no longer triggered an immune reaction. Such peptides can be used both for the therapy of already existing *Clostridium difficile* diseases and for protection against such diseases in human and veterinary medicine.

The hitherto existing scientific results can be summarised in that, on the one hand, the toxin A of *Clostridium difficile* is able to trigger the full symptoms of pseudomembranous colitis (PMC) and on the other hand that the monoclonal antibody TTC8 directed against this toxin can neutralise the effect of this toxin during in vivo experiments (in mice). The mAb TTC8 is an antibody of the class IgG 2b. The specific recognition between mAb TTC8 and toxin A of *Clostridium difficile* is mediated by the hypervariable regions of the heavy and light chains. This means that exactly defined sections of the antibody (in other words, peptides) are responsible for antigen recognition. Knowledge of the hypervariable regions makes it possible to copy these peptides (structures) to antibody sequences of other species, which are then suitable for therapy and prophylaxis of *Clostridium difficile* diseases, for example in the form of humanised monoclonal antibodies in humans, without having the undesirable side effects of the species-foreign antibodies usually obtained from mice.

It was therefore necessary to determine the nucleotide sequences and the deduced amino acid sequences of the hypervariable, toxin-neutralising monoclonal antibody, so as to be able to use it in the form of peptide sections or humanised antibodies (incorporated into the human antibody gene) for therapy and prophylaxis in humans. A thorough sequencing determination of this type was for example carried out on the cell DSM 2322, which produces the monoclonal antibody TTC8. This antibody neutralises the biological action of enterotoxin A by blocking its ligand domains.

As an example, the hypervariable and variable peptide sequences, which exert the neutralising effect of mAb TTC8, were determined for cell line DSM ACC 2322 with sequences SEQ ID No. 1–12 and/or SEQ ID No. 13–16. Knowledge of the variable regions of neutralising antibodies enables peptides to be produced which block the biological action of *Clostridium difficile* by binding to its enterotoxin and/or cytotoxin. These peptide sequences, such as SEQ ID No. 14 and/or SEQ ID No. 16 of the sequence protocol, can be used as such or can be incorporated into the immunoglobulin as a therapy for *Clostridium difficile* diseases. For therapeutic use in humans, human immunoglobulin is used; for use in veterinary medicine, incorporation of the sequences must be carried out into the immunoglobulin gene of the species being treated.

Derivatives of such peptides can be produced, while still preserving their biological activity, by amino acid deletion, insertion, addition or replacement, i.e. by allelic variation. These derivatives, like the original peptides, can inhibit the biological activity of *Clostridium difficile* through binding to its enterotoxin and/or cytotoxin and can thus be used for the therapy and prophylaxis of *Clostridium difficile* diseases.

The following named hypervariable regions (CDRs= complementarity determining regions) were determined in mAb TTC8 isolated from hybridoma cell line DSM ACC 2322 deposited in the German collection of microorganisms and cell cultures (DSMZ). They show the following amino acid sequences:

CDRs of the heavy chain:
    CDR-1: -Asn-Tyr-Trp-Met-Asn-(SEQ ID No. 2)
    CDR-2: -Arg-Ile-Tyr-Pro-Gly-Asp-Gly-Asp-Ala-His-Tyr-Asn-Gly-Lys-Phe-Lys-Gly-(SEQ ID No. 4)
    CDR-3: -Gly-Gly-Asn-Tyr-Asp-Asp-Arg-Val-Phe-Asp-Tyr-(SEQ ID No. 6)
CDRs of the light chain:
    CDR-4: -Lys-Ala-Ser-Gln-Asn-Val-Gly-Thr-Asn-Val-Ala-(SEQ ID No. 8)
    CDR-5: -Ser-Pro-Ser-Tyr-Arg-Tyr-Ser-(SEQ ID No. 10)
    CDR-6: -Gln-Gln-Tyr-Asn-Ser-Tyr-Pro-Leu-Thr-(SEQ ID No. 12)

The following procedure was adopted for the determination of these sequences: First the total RNA of the hybridoma cell, which produce the mAb TTC8, was prepared according to a known procedure. The mRNA was then separated in a second step. This was carried out with the help of magnetic polystyrene beads to which the oligo(dT)$_{25}$ chains are covalently attached.

From the purified mRNA, cDNA was then synthesized and with the help of the polymerase chain reaction (PCR), the VH- and VL-gene of mAb TTC8, which code for the light (VL) or heavy (VH) chain of the TTC8 antibody, were amplified. It was here of decisive importance that primers were selected which showed a suitable restriction site so as to facilitate the subsequent cloning.

The VH- and VL-genes of mAb TTC8 thus produced were subsequently cloned in vector pUC 19 and then sequenced. In this way the nucleotide sequences (SEQ ID No. 13 and 15) and the derived amino acid sequences corresponding to SEQ ID No. 14 and SEQ ID No. 16 were determined.

The hypervariable regions can be identified by means of a comparison with the germ line gene V 102. From the gene of the heavy chain (SEQ ID No. 13) it can be seen that the CDR-1 of the heavy chain contains 5 amino acids and begins at position 30 of the sequence. The CDR-2 of the heavy chain begins at position 49 and contains 17 amino acids. The hypervariable region CDR-3 begins at position 98 and contains 11 amino acids.

Altogether the VH-gene of mAb TTC8 shows 36 point mutations compared to germ line gene V 102. Three of the mutations lie in the binding region of the PCR primer and may therefore be caused by the sequence of the primer. Almost all mutations in the hypervariable regions lead to a change in the amino acid sequence, while nearly half of all mutations in the framework region are inactive.

In the gene for the light chain (SEQ ID No. 15), the hypervariable regions could be established as follows: the CDR-4 begins at position 22 and contains 11 amino acids. The CDR-5 contains 7 amino acids and begins at position 48. The CDR-6 begins at position 87 and contains 9 amino acids. The VL-gene of mAb TTC8 compared to mAb A23 shows only 9 mutations. Of these, 4 lie in the binding region of the PCR primer. Of the five remaining differences in the nucleotide sequence, two mutations are inactive on the protein level. Of the mutations which lead to a change in the amino acid sequence, one lies in the CDR-4, the other two are both in the framework regions 2 and 3.

In a corresponding way, using the hybridoma cell line deposited at the DSMZ (German collection of microorganisms and cell cultures) under number DSM ACC 2321, it is possible to determine the sequences of the hypervariable regions of the monoclonal antibody which recognise the cytotoxin (toxin B) of *Clostridium difficile*.

The therapeutic use of a monoclonal antibody derived from mice causes an immune reaction in humans. In order to overcome this problem, an antibody can be adapted (i.e. humanised) to the species to be treated (here humans). There are several procedures for this, which amount to replacing the immunogenic portion of the murine monoclonal antibody with a corresponding portion of a human antibody. They are known from, for example, European patent applications 184 187, 171 496 and 173 494.

The humanised monoclonal antibodies produced from a procedure of this type are considerable more suitable for therapeutic use in humans than the antibodies produced from mice.

These methods for humanising antibodies can also be used for mAb TTC8 and other toxin A and toxin B neutralising monoclonal antibodies. They produce a humanised monoclonal antibody which forms a chimera from the hypervariable regions (e.g. for TTC8: SEQ ID No. 1–12) of the neutralising mAb TTC8 inserted in the framework region of a human immunoglobulin. The latter can be of subtype IgG (preferred for parenteral application) or subtype IgA (preferred for peroral application). As described for the TTC8 antibodies (from the DSM ACC 2322 cell line), the hypervariable regions of other monoclonal antibodies directed against *Clostridium difficile* can be cloned in a corresponding way, sequenced and used for the production of humanised antibodies.

A further object of the invention are humanised monoclonal antibodies in which the amino acid sequence is modified through allelic variations within the variable and/or constant regions of the light and/or heavy chains of human immunoglobulin, as long as the binding ability to *Clostridium difficile* toxin A and/or toxin B is maintained.

All the biological "building blocks" necessary for the production of monoclonal antibodies according to the invention, such as cell lines, plasmids, promoters, resistance markers, origins of replication, and other fragments of vectors, insofar as they are not deposited as here described, are obtainable on the market or are generally available. If not otherwise stated, they are only used as examples and are not crucial for carrying out the invention, but can be replaced by other suitable biological "building blocks". Bacterial cells are preferably used as hosts for the amplification of the named DNA sequences according to the invention. Examples for this are *E. coli* or Bacillus spec.

The production of humanised antibodies can be carried out in eukaryote cells such as yeast cells, fungi or, for example, CHO (Chinese hamster ovary cells). The production in plants can be carried out in monocotyledons or dicotyledons.

As an example, the production of antibodies in plants is described below. Production in other organisms is carried out in an analogous way.

The production of specified antibodies in plants is already known from [2] and from international patent application WO 91/06320. For the production of the monoclonal antibody in transgenic plants, the genes for the complete monoclonal antibody or for its recombinant derivatives are cloned, or the gene for a single chain antibody under the control of one or two plant-active promoters in a plant transformation vector is cloned.

The final transformation vector contains all the DNA sequences to be transferred into the plant. These are transferred from the vector into the plant cells. Alternatively the genes for the light and the heavy chains can also be separately incorporated in two plant transformation vectors and separately transferred into plant cells, so as to only later join them together in the final antibody construct. The transformation of plants can be carried out with any suitable method, for example with the help of *Agrobacterium tumefaciens* or through direct gene transfer or with the help of a gene gun.

The production of antibodies can be directed into predetermined compartments of the cell. By removing the coding sequence for the signal peptide, the antibodies are expressed cytoplasmatically. For high expression of the antibodies, a DNA sequence is connected to the 5'-end of the gene or the naturally occurring one is left, which codes for a signal peptide for transport into the endoplasmic reticulum. In order to obtain specific localisation in a defined cell compartment, it is possible to fuse, onto or into the gene, the DNA sequences which code for the peptide sequences responsible for it. Through integration of a KDEL-sequence it is possible, for example, to secure retention in the endoplasmic reticulum.

The incorporation of the antibody gene into the transgenic gene is analysed and confirmed through suitable restriction digestion of the isolated genomic plant DNA and subsequent Southern hybridisation. Transcription of the gene can be demonstrated using the Northern blot procedure. The biosynthesized antibody is detected using, for example, a specific secondary polyclonal or monoclonal antibody in plant extracts or with a polyclonal or monoclonal antibody directed against the constant region or against a tag-sequence specially introduced for this purpose.

Both monocotyledons, such as barley and wheat, and dicotyledons, such as potatoes, rape, carrots or peas, are suitable as production plants. The expression of the antibody can occur in various organs of the plant, for example in leaves, seeds, tubers or other tissue.

Purification of the antibody expressed in the plant is carried out using, for example, chromatographic methods that are usually also used for purifying antibodies from hybridoma cell lines. Furthermore, recombinant antibodies containing a tag sequence can also be purified by means of specially established affinity chromatography methods such as metal chelation chromatography.

The humanised monoclonal antibodies of the invention can be administered to the human patient for the therapy and prophylaxis of *Clostridium difficile* caused diseases following known methods. In general the antibodies or antibody fragments of the invention are administered parenterally, or preferably perorally. The direct peroral taking of plants containing the antibodies as raw food can be considered as a special "galenic preparation". The appropriate dosage of the antibodies of the invention is to be adjusted for the relevant patient and is dependent, for example, on the patient's body weight, age and disease status. The dosage is set by an experienced medical doctor and usually lies between 0.1 mg/kg and 70 mg/kg, administered once or several times per day over a period of several days.

EXAMPLES

Example 1

Isolation of Total RNA of Hybridoma Cells Which Produce mAb TTC8 (DSM ACC 2322)

For the production of RNA by CsCl gradients, the cells are initially broken down by guanidine thiocyanate buffer and then completely disrupted mechanically, with the help of an Ultrathorax. Cell debris is centrifuged off and the solution added on top of a pre-prepared CsCl cushion (5.7 M). During the following centrifugation the RNA forms a pellet at the bottom of the test tube. This bottom layer is separated off using a hot scalpel and the pellet dissolved by adding $H_2O$. The RNA is then further purified by precipitation from the solution. It is finally dissolved in 100 µl $H_2O$. The concentration of the RNA thus prepared usually lies in the range 1.5–3 µg/µl.

Example 2

Isolation of the mRNA

For the purification of the mRNA from the other RNA species, it was hybridised to oligo(dT)$_{25}$ beads according to the method described by Dynal. The binding capacity of the beads is 2 µg RNA per mg of beads. The proportion of mRNA to total RNA is about 1–5%, so 1 mg beads was added to 80 µg total RNA. Purification proceeded according to the method of Dynal Company with the following alteration. The bound mRNA was washed twice with a buffer containing 10 mM Tris/HCl (pH 7.5), 0.15 mM LiCl, 1 mM EDTA, 1% SDS and then washed twice with an altered buffer having lower salt concentration [5 mM Tris/HCl (pH 7.5), 75 mM LiCl, 0.5 mM EDTA]. All further steps matched the Dynal specifications. The addition of SDS and the additional washing step at lower salt concentration (more stringent) considerably improved the purity of the mRNA.

Example 3

Synthesis of cDNA

From the purified mRNA, cDNA was synthesized using MMLV-reverse transcriptase (Moloney murine leukemia virus). In the experiment oligo(dT)$_{12-18}$ primer was used in 2-fold excess in order to maintain high the proportion of hybridised mRNA-oligo(dT) molecules. The concentration of nucleotide triphosphates was higher than 1 mM during the reaction. Premature increased breakdown of the RNA in solution was counteracted by addition of human and placental ribonuclease inhibitor. The ssDNA thus produced was used in the PCR reactions for amplification of the variable regions of the mAb TTC8.

Example 4

Polymerase Chain Reaction for Amplification of the cDNA

The amplification of the cDNA was carried out according to the known method of European patent 0 388 914. From a range of publications, particular primers for PCR amplification of the variable regions of mice monoclonal antibodies were deduced. These were:

Heavy chain: (an introduced Sal1 restriction site is underlined)
  VH5Prim: 5'-AG GTCGACCTGCAG(C/G)AGTC(A/T)GG-3'(SEQ ID No. 18);
  VH3Prim: 5'-ACGGTGACA GTCGACCCTTGGCCCC-3'(SEQ ID No. 19);

Light chain: (an introduced Sac1 restiction site is underlined)
  VL5Prim: 5'-GACATT GAGCTCACCCAGTCTCCA-3'(SEQ ID No. 20);
  VL3Prim: 5'-GTTT GAGCTCCAGCTTGGTCCC-3'(SEQ ID No. 21).

The optimal primer concentration for the production of the variable regions was 0.5 µM, the dNTPs were used at a final concentration of 400 µM.

PCR temperatures were established as a second significant parameter. For the amplification of the VH-region the reaction sequence was as follows: denaturing 1 min. 92°; annealing 1.5 min. 50°; elongation 3 min. 72° for 30 cycles. For the VL-amplification the reaction sequence was as follows: denaturing 1 min. 92°; annealing 1.5 min. 60°; elongation 3 min. 72° for 30 cycles.

Example 5

Cloning of the VH- and VL-Gene of mAb TTC8

For cloning, the PCR products were cut with Sal1 (VH) or Sac1 (VL) and purified over agarose gel. Cloning into pUC19 was performed into the homologous restriction sites.

As the desired clones, the constructs pVHT8 and pVLT8.10 were identified by control digestion. They contain the VH- or VL-segments with positive orientation relative to the pLac promoter of pUC19.

Example 6

Sequencing of the Variable Domains of mAb TTC8

The insert of pVHT8 has a size of 341 bp, the insert of clone pVLT8.10 is 312 bp. Both clones possess an open reading frame which extends over the whole insert. The sequences of PCR primers and the cutting sites can be well identified.

By sequence comparison, the relation of VH-segments to the multigene family J558 can be found. The highest degree of homology was to the germ line sequence V102.

The gene for the VL-region of mAb TTC8 has 94% homology to a sequence of an antibody which is attributed to the germ line gene Vk19d. Accordingly the VL-region of TTC8 is also to be related to this gene family.

Example 7

Production of a Humanised Monoclonal Antibody

In order to prevent a reaction of the human immune system when applying antibodies of other species (henceforth referred to as non-human), the immunogenic regions of the mAb must be replaced by homologous human sequences. There are basically two possibilities for this:

a) the creation of chimeric mouse/human antibodies, in which the variable antigen-determining region of the chimeric antibody originates from non-human antibodies and the constant region originates from human antibodies.

b) the complete humanisation of the mAb. According to this approach also the framework regions in the variable region of mAb are replaced by corresponding human sequences and only the CDR regions are retained in the original form or as allelic variants.

For carrying out the work in practice, a range of methods can be adopted. They are well documented and known by experts in the field.

to a) Chimeric antibodies are produced by coupling the sequences of the constant regions of a human antibody to the sequences of the variable region of non-human mAb, in a suitable vector system. A complete chimeric antibody can be produced, or only a part of the chimeric antibody, the so called Fab fragment [3]. The production of chimeric antibodies has the advantage that the method is relatively problem free. The antibodies produced show slightly increased immunogenicity due to the remaining mouse portions in the protein, but these are of minor importance following oral application.

to b) For the complete humanisation of non-human mAb, a human antibody whose structure approximately corresponds to that of the original antibody is first identified through sequence comparison and 3D modelling. Then, by subsequent rounds of PCR amplifications, a complete humanised gene for the variable portion of the antibodies is generated [4], using five oligonucleotide primers that bind to the sequence of the variable regions of human antibodies (VL or VH) in combination with three oligonucleotides that encode the sequences of the CDR regions of the mouse antibody. A second modified approach is to assemble the gene from several synthetic, overlapping oligonucleotides that code for the target sequence (for strategy and procedure cf. [4]). Alternatively, it is possible after identification of a homologous human antibody, to adjust just the amino acids in which the framework regions of both antibodies differ, by site directed mutagenesis, [5]. Antibodies modified in this way can succumb to an alteration in their specificity to be adjusted by reverse mutation [5]. The complete humanisation of antibodies by the last named procedure is relatively demanding, but these antibodies produce practically no immune response in humans [6].

Bibliography

[1] Eichel-Streiber, C. V., P. Boquet, M. Sauerborn and M. Thalestam. 1996. Large clostridial cytotoxins—a family of glycosyltransferases modifying small GTP-binding proteins. Trends in Microbiology, 14: 375–382.

[2] Düring, K. (1988) "Wundinduzierte Expression und Sekretion von T4 Lysozym und Monoklonalen Antikörpern in *Nicotiana tabacum*." Ph.D. Thesis, Universität Köln.

[3] Skerra, A. (1994). A general vector, pASK 84 for cloning, bacterial production and single step purification of antibody Fab fragments. Gene 141: 79–84.

[4] Sato, K., M. Tsuchiya, J. Saldanha, Y. Koishihara, Y. Ohsugi, T. Kishimoto and M. M. Bendig (1994). Humanization of a mouse anti-human Interleukin-6 receptor antibody comparing two methods for selecting human framework regions. Mol. Immun. 31: 371–381.

[5] Benhar I., E. A. Padlan, S. H. Lee, B. Lee and I. Pastan (1994). Rapid humanization of the Fv of monoclonal antibody B3 by using framework exchange of the recombinant immunotoxin B3(Fv)-PE38. Proc. Natl. Acad. Sci. USA 91:12051–12055.

[6] Stephens S., S. Emtage, 0. Vetterlein, L. Chaplin, C. Bebbington, A. Nesbitt, M. Sopwith, D. Athwal, C. Nowak and M. Bodmer (1995). Comprehensive pharmacokinetics of a humanized antibody and analysis of residual anti-idiotypic responses. Immunology 85: 668–674.

What is claimed is:

1. An isolated polypeptide, the amino acid sequence of which comprises a sequence including the peptide sequences of SEQ ID NO: 2, 4, 6, 8, 10, and 12, and wherein said polypeptide specifically binds *Clostridium difficile* enterotoxin (toxin A).

2. The polypeptide of claim 1, wherein said polypeptide is capable of forming a variable or hypervariable antigen-binding domain (region) of a monoclonal antibody that specifically binds *Clostridium difficile* enterotoxin (toxin A).

3. The polypeptide of claim 1, wherein said polypeptide neutralizes the biological activity of *Clostridium difficile* enterotoxin (toxin A).

4. An isolated polypeptide, the amino acid sequence of which comprises a sequence including the peptide sequences of SEQ ID NOS: 2, 4, and 6, wherein said polypeptide specifically binds *Clostridium difficile* enterotoxin (toxin A).

5. The polypeptide of claim 4, wherein said polypeptide forms a variable or hypervariable antigen-binding domain (region) of a monoclonal antibody that specifically binds *Clostridium difficile* enterotoxin (toxin A).

6. The polypeptide of claim 4, wherein said polypeptide neutralizes the biological activity of *Clostridium difficile* enterotoxin (toxin A).

7. An isolated polypeptide, the amino acid sequence of which comprises a sequence including the peptide sequences of SEQ ID NOS: 8, 10, and 12, wherein said polypeptide specifically binds *Clostridium difficile* enterotoxin (toxin A).

8. The polypeptide of claim 7, wherein said polypeptide forms a variable or hypervariable antigen-binding domain (region) of a monoclonal antibody that specifically binds *Clostridium difficile* enterotoxin (toxin A).

9. The polypeptide of claim 7, wherein said polypeptide neutralizes the biological activity of *Clostridium difficile* enterotoxin (toxin A).

10. An isolated polypeptide composition comprising a first polypeptide and a second polypeptide, where said first polypeptide comprises a sequence including the peptide sequences of SEQ ID NO: 2, 4, and 6, and said second polypeptide comprises a sequence including the peptide sequences of SEQ ID NO: 8, 10, and 12, and wherein said first polypeptide and said second polypeptide specifically binds *Clostridium difficile* enterotoxin (toxin A).

11. The polypeptide composition of claim 10, wherein said first polypeptide and said second polypeptide form a variable or hypervariable antigen-binding domain (region) of a monoclonal antibody that specifically binds *Clostridium difficile* enterotoxin (toxin A).

12. The polypeptide composition of claim 10, wherein said first polypeptide and said second polypeptide neutralizes the biological activity of *Clostridium difficile* enterotoxin (toxin A).

13. A method of neutralizing *Clostridium difficile* enterotoxin, comprising contacting said enterotoxin to the polypeptide of claim 1.

14. A method of neutralizing *Clostridium difficile* enterotoxin, comprising contacting said enterotoxin to the polypeptide of claim 4.

15. A method of neutralizing *Clostridium difficile* enterotoxin, comprising contacting said enterotoxin to the polypeptide of claim 7.

16. A method of neutralizing *Clostridium difficile* enterotoxin, comprising contacting said enterotoxin to the polypeptide composition of claim 10.

* * * * *

SEQUENCE LISTING

```
<160> NUMBER OF SEQ ID NOS: 21

<210> SEQ ID NO 1
<211> LENGTH: 15
<212> TYPE: DNA
<213> ORGANISM: Mus musculus
<220> FEATURE:
<221> NAME/KEY: misc_feature
<222> LOCATION: (1)...(15)
<223> OTHER INFORMATION: heavy chain CDR1
<221> NAME/KEY: CDS
<222> LOCATION: (1)...(15)

<400> SEQUENCE: 1 aac tac tgg atg aac                                              15
Asn Tyr Trp Met Asn
 1               5

<210> SEQ ID NO 2
<211> LENGTH: 5
<212> TYPE: PRT
<213> ORGANISM: Mus musculus

<400> SEQUENCE: 2

Asn Tyr Trp Met Asn
 1               5

<210> SEQ ID NO 3
<211> LENGTH: 51
<212> TYPE: DNA
<213> ORGANISM: Mus musculus
<220> FEATURE:
<221> NAME/KEY: misc_feature
<222> LOCATION: (1)...(51)
```

```
<223> OTHER INFORMATION: Heavy chain CDR2
<221> NAME/KEY: CDS
<222> LOCATION: (1)...(51)

<400> SEQUENCE: 3 cgg att tat cct gga gat gga gat gct cac tac aat ggg aag ttc aag        48
Arg Ile Tyr Pro Gly Asp Gly Asp Ala His Tyr Asn Gly Lys Phe Lys
  1               5                  10                  15 ggc                                                                     51
Gly

<210> SEQ ID NO 4
<211> LENGTH: 17
<212> TYPE: PRT
<213> ORGANISM: Mus musculus

<400> SEQUENCE: 4

Arg Ile Tyr Pro Gly Asp Gly Asp Ala His Tyr Asn Gly Lys Phe Lys
  1               5                  10                  15

Gly

<210> SEQ ID NO 5
<211> LENGTH: 33
<212> TYPE: DNA
<213> ORGANISM: Mus musculus
<220> FEATURE:
<221> NAME/KEY: misc_feature
<222> LOCATION: (1)...(33)
<223> OTHER INFORMATION: Heavy chain CDR3
<221> NAME/KEY: CDS
<222> LOCATION: (1)...(33)

<400> SEQUENCE: 5 ggg ggg aat tac gac gac agg gtc ttt gac tac                             33
Gly Gly Asn Tyr Asp Asp Arg Val Phe Asp Tyr
  1               5                  10

<210> SEQ ID NO 6
<211> LENGTH: 11
<212> TYPE: PRT
<213> ORGANISM: Mus musculus

<400> SEQUENCE: 6

Gly Gly Asn Tyr Asp Asp Arg Val Phe Asp Tyr
  1               5                  10

<210> SEQ ID NO 7
<211> LENGTH: 33
<212> TYPE: DNA
<213> ORGANISM: Mus musculus
<220> FEATURE:
<221> NAME/KEY: misc_feature
<222> LOCATION: (1)...(33)
<223> OTHER INFORMATION: Hypervariable region (CDR) light chain
<221> NAME/KEY: CDS
<222> LOCATION: (1)...(33)

<400> SEQUENCE: 7 aag gcc agt cag aat gtg ggt act aat gta gcc                             33
Lys Ala Ser Gln Asn Val Gly Thr Asn Val Ala
  1               5                  10

<210> SEQ ID NO 8
<211> LENGTH: 11
<212> TYPE: PRT
<213> ORGANISM: Mus musculus
```

```
<400> SEQUENCE: 8

Lys Ala Ser Gln Asn Val Gly Thr Asn Val Ala
 1               5                  10

<210> SEQ ID NO 9
<211> LENGTH: 21
<212> TYPE: DNA
<213> ORGANISM: Mus musculus
<220> FEATURE:
<221> NAME/KEY: misc_feature
<222> LOCATION: (1)...(21)
<223> OTHER INFORMATION: Light chain CDR2
<221> NAME/KEY: CDS
<222> LOCATION: (1)...(21)

<400> SEQUENCE: 9 tcg cca tcc tac cgg tac agt                                          21
Ser Pro Ser Tyr Arg Tyr Ser
 1               5

<210> SEQ ID NO 10
<211> LENGTH: 7
<212> TYPE: PRT
<213> ORGANISM: Mus musculus

<400> SEQUENCE: 10

Ser Pro Ser Tyr Arg Tyr Ser
 1               5

<210> SEQ ID NO 11
<211> LENGTH: 27
<212> TYPE: DNA
<213> ORGANISM: Mus musculus
<220> FEATURE:
<221> NAME/KEY: misc_feature
<222> LOCATION: (1)...(27)
<223> OTHER INFORMATION: Heavy chain CDR3
<221> NAME/KEY: CDS
<222> LOCATION: (1)...(27)

<400> SEQUENCE: 11 cag caa tat aat agc tat cct ctt acg                                  27
Gln Gln Tyr Asn Ser Tyr Pro Leu Thr
 1               5

<210> SEQ ID NO 12
<211> LENGTH: 9
<212> TYPE: PRT
<213> ORGANISM: Mus musculus

<400> SEQUENCE: 12

Gln Gln Tyr Asn Ser Tyr Pro Leu Thr
 1               5

<210> SEQ ID NO 13
<211> LENGTH: 341
<212> TYPE: DNA
<213> ORGANISM: Mus musculus
<220> FEATURE:
<221> NAME/KEY: misc_feature
<222> LOCATION: (1)...(341)
<223> OTHER INFORMATION: Variable region VH of heavy chain
<221> NAME/KEY: CDS
<222> LOCATION: (1)...(341)
<221> NAME/KEY: primer_bind
<222> LOCATION: (1)...(21)
<223> OTHER INFORMATION: /label=VH5PRIM
<221> NAME/KEY: primer_bind
<222> LOCATION: (325)...(341)
```

<223> OTHER INFORMATION: /label=VH3PRIM

<400> SEQUENCE: 13

```
gtc gac ctg cag cag tct gga cct gag ctg gtg aag cct ggg gcc tca        48
Val Asp Leu Gln Gln Ser Gly Pro Glu Leu Val Lys Pro Gly Ala Ser
 1               5                  10                  15 gtg aag att tcc tgc aaa gct tct ggc tac gca ttc agt aac tac tgg        96
Val Lys Ile Ser Cys Lys Ala Ser Gly Tyr Ala Phe Ser Asn Tyr Trp
            20                  25                  30 atg aac tgg gtg aag cag agg cct gga aag ggt ctt gag tgg att gga       144
Met Asn Trp Val Lys Gln Arg Pro Gly Lys Gly Leu Glu Trp Ile Gly
        35                  40                  45 cgg att tat cct gga gat gga gat gct cac tac aat ggg aag ttc aag       192
Arg Ile Tyr Pro Gly Asp Gly Asp Ala His Tyr Asn Gly Lys Phe Lys
    50                  55                  60 ggc aag gcc aca ctg act gca gac aaa tcc tcc agc aca gcc tac atg       240
Gly Lys Ala Thr Leu Thr Ala Asp Lys Ser Ser Ser Thr Ala Tyr Met
65                  70                  75                  80 caa ctc agc agc ctg aca tct gag gac tct gcg gtc tac ttc tgt gca       288
Gln Leu Ser Ser Leu Thr Ser Glu Asp Ser Ala Val Tyr Phe Cys Ala
                85                  90                  95 aga ggg ggg aat tac gac gac agg gtc ttt gac tac tgg ggc caa ggg       336
Arg Gly Gly Asn Tyr Asp Asp Arg Val Phe Asp Tyr Trp Gly Gln Gly
                100                 105                 110 tcg ac                                                                341
Ser
```

<210> SEQ ID NO 14
<211> LENGTH: 113
<212> TYPE: PRT
<213> ORGANISM: Mus musculus

<400> SEQUENCE: 14

```
Val Asp Leu Gln Gln Ser Gly Pro Glu Leu Val Lys Pro Gly Ala Ser
 1               5                  10                  15

Val Lys Ile Ser Cys Lys Ala Ser Gly Tyr Ala Phe Ser Asn Tyr Trp
            20                  25                  30

Met Asn Trp Val Lys Gln Arg Pro Gly Lys Gly Leu Glu Trp Ile Gly
        35                  40                  45

Arg Ile Tyr Pro Gly Asp Gly Asp Ala His Tyr Asn Gly Lys Phe Lys
    50                  55                  60

Gly Lys Ala Thr Leu Thr Ala Asp Lys Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95

Arg Gly Gly Asn Tyr Asp Asp Arg Val Phe Asp Tyr Trp Gly Gln Gly
                100                 105                 110

Ser
```

<210> SEQ ID NO 15
<211> LENGTH: 312
<212> TYPE: DNA
<213> ORGANISM: Mus musculus
<220> FEATURE:
<221> NAME/KEY: misc_feature
<222> LOCATION: (1)...(312)
<223> OTHER INFORMATION: Variable region of the light chain
<221> NAME/KEY: CDS
<222> LOCATION: (1)...(312)
<221> NAME/KEY: primer_bind
<222> LOCATION: (1)...(18)

<223> OTHER INFORMATION: /label=VL5Prim
<221> NAME/KEY: primer_bind
<222> LOCATION: (289)...(312)
<223> OTHER INFORMATION: /label=VL3Prim

<400> SEQUENCE: 15

```
gag ctc acc cag tct cca aaa ttc atg tcc aca tca gta gga gac agg      48
Glu Leu Thr Gln Ser Pro Lys Phe Met Ser Thr Ser Val Gly Asp Arg
 1               5                  10                  15 gtc agc gtc acc tgc aag gcc agt cag aat gtg ggt act aat gta gcc      96
Val Ser Val Thr Cys Lys Ala Ser Gln Asn Val Gly Thr Asn Val Ala
             20                  25                  30 tgg tat caa cag aaa cca ggg caa tct cct aaa aca ctg att tac tcg     144
Trp Tyr Gln Gln Lys Pro Gly Gln Ser Pro Lys Thr Leu Ile Tyr Ser
         35                  40                  45 cca tcc tac cgg tac agt gga gtc cct gat cgc ttc aca ggc agt gga     192
Pro Ser Tyr Arg Tyr Ser Gly Val Pro Asp Arg Phe Thr Gly Ser Gly
     50                  55                  60 tct ggg aca gat ttc act ctc acc atc agc aat gtg cag tct gtt gac     240
Ser Gly Thr Asp Phe Thr Leu Thr Ile Ser Asn Val Gln Ser Val Asp
 65                  70                  75                  80 ttg gca gag tat ttc tgt cag caa tat aat agt tat cct ctt acg ttc     288
Leu Ala Glu Tyr Phe Cys Gln Gln Tyr Asn Ser Tyr Pro Leu Thr Phe
                 85                  90                  95 ggc tcg ggg acc aag ctg gag ctc                                     312
Gly Ser Gly Thr Lys Leu Glu Leu
            100
```

<210> SEQ ID NO 16
<211> LENGTH: 104
<212> TYPE: PRT
<213> ORGANISM: Mus musculus

<400> SEQUENCE: 16

```
Glu Leu Thr Gln Ser Pro Lys Phe Met Ser Thr Ser Val Gly Asp Arg
 1               5                  10                  15

Val Ser Val Thr Cys Lys Ala Ser Gln Asn Val Gly Thr Asn Val Ala
             20                  25                  30

Trp Tyr Gln Gln Lys Pro Gly Gln Ser Pro Lys Thr Leu Ile Tyr Ser
         35                  40                  45

Pro Ser Tyr Arg Tyr Ser Gly Val Pro Asp Arg Phe Thr Gly Ser Gly
     50                  55                  60

Ser Gly Thr Asp Phe Thr Leu Thr Ile Ser Asn Val Gln Ser Val Asp
 65                  70                  75                  80

Leu Ala Glu Tyr Phe Cys Gln Gln Tyr Asn Ser Tyr Pro Leu Thr Phe
                 85                  90                  95

Gly Ser Gly Thr Lys Leu Glu Leu
            100
```

<210> SEQ ID NO 17
<211> LENGTH: 9
<212> TYPE: PRT
<213> ORGANISM: Mus musculus

<400> SEQUENCE: 17

```
Thr Ile Asn Gly Lys Lys Tyr Tyr Phe
 1               5
```

<210> SEQ ID NO 18
<211> LENGTH: 22
<212> TYPE: DNA

```
<213> ORGANISM: Mus musculus
<220> FEATURE:
<221> NAME/KEY: misc_feature
<222> LOCATION: (1)...(22)
<223> OTHER INFORMATION: Variable region of the heavy chain/VH5Prim

<400> SEQUENCE: 18
aggtcgacct gcagsagtcw gg                                              22

<210> SEQ ID NO 19
<211> LENGTH: 25
<212> TYPE: DNA
<213> ORGANISM: Mus musculus
<220> FEATURE:
<221> NAME/KEY: misc_feature
<222> LOCATION: (1)...(25)
<223> OTHER INFORMATION: Variable region of the heavy chain/VH3Prim

<400> SEQUENCE: 19
acggtgacag tcgaccttg gcccc                                            25

<210> SEQ ID NO 20
<211> LENGTH: 24
<212> TYPE: DNA
<213> ORGANISM: Mus musculus
<220> FEATURE:
<221> NAME/KEY: misc_feature
<222> LOCATION: (1)...(24)
<223> OTHER INFORMATION: Variable region of the light chain/VL5Prim

<400> SEQUENCE: 20
gacattgagc tcacccagtc tcca                                            24

<210> SEQ ID NO 21
<211> LENGTH: 22
<212> TYPE: DNA
<213> ORGANISM: Mus musculus
<220> FEATURE:
<221> NAME/KEY: misc_feature
<222> LOCATION: (1)...(22)
<223> OTHER INFORMATION: Variable region of the light chain/VL3Prim

<400> SEQUENCE: 21
gtttgagctc cagcttggtc cc                                              22
```